United States Patent [19]

Pellico

[11] Patent Number: 4,515,913

[45] Date of Patent: May 7, 1985

[54] DENTAL IMPRESSION COMPOSITION

[75] Inventor: Michael A. Pellico, Los Angeles, Calif.

[73] Assignee: Laclede Professional Products, Inc., Gardena, Calif.

[21] Appl. No.: 550,809

[22] Filed: Nov. 14, 1983

Related U.S. Application Data

[63] Continuation-in-part of Ser. No. 490,294, May 2, 1983, Pat. No. 4,468,484, which is a continuation-in-part of Ser. No. 378,917, May 17, 1982, Pat. No. 4,381,947, which is a continuation-in-part of Ser. No. 220,303, Dec. 29, 1980, abandoned.

[51] Int. Cl.$^3$ .............................................. A61K 6/08
[52] U.S. Cl. ..................................... 523/109; 106/35; 106/207; 106/209; 260/998.11; 524/28; 433/214
[58] Field of Search ......................... 523/109; 524/28; 106/35, 38.5 D, 207, 209; 260/998.11; 433/214

[56] References Cited

U.S. PATENT DOCUMENTS

| | | | |
|---|---|---|---|
| 3,970,629 | 7/1976 | Izaki et al. | 524/28 |
| 4,113,854 | 9/1978 | Andrews et al. | 524/28 |
| 4,154,910 | 5/1979 | Tanaka et al. | 526/303.1 |

Primary Examiner—Lorenzo B. Hayes
Attorney, Agent, or Firm—Donald Diamond

[57] ABSTRACT

Powdered alginate compositions formulated with a polymer comprising polyacrylamide have enhanced smoothness characteristics upon admixing with water to obtain orally settable, dental impression material.

11 Claims, No Drawings

4,515,913

DENTAL IMPRESSION COMPOSITION

CROSS-REFERENCE TO RELATED APPLICATIONS

This application is a continuation-in-part of U.S. patent application Ser. No. 490,294, filed May 2, 1983, now U.S. Pat. No. 4,468,484, for Settable Alignate Compositions Containing Polyacrylamide, which application, in turn, is a continuation-in-part of U.S. patent application Ser. No. 378,917, filed May 17, 1982, for Settable Alginate Compositions, (now U.S. Pat. No. 4,381,947), which application, in turn, is a continuation-in-part of U.S. patent application Ser. No. 220,303, filed Dec. 29, 1980, now abandoned.

BACKGROUND OF THE INVENTION

This invention relates to dental preparations and, more particularly, to powdered alginate compositions which are adapted to be admixed with water to provide orally settable, dental impression material.

Alginate compositions have long been used in dentistry as impression material for making impressions in areas in which partial dentures are to be constructed, for fabricating study models in orthodontic treatment, for making primary impressions in endentulous mouths, and as corrective materials in secondary impressions of all types.

As distinguished from agar-based thermally reversible hydrocolloids which gel by lowering the temperature of the heated and fluidized material, alginate compositions gel by means of a chemical reaction. After the alginate gel is formed, it cannot be converted to a fluid condition or sol by physical means and, thus, the alginates are known as irreversible hydrocolloids. The use of alginates in dental therapeutics is reviewed in the text entitled *Elements of Dental Materials,* by Ralph Phillips at Chapter 9.

Alginate compositions designed for use in dental therapeutics are typically formulated as powders which are adapted to be mixed with water to form a viscous sol. The sol is carried into the mouth in a perforated impression tray where it forms an elastic gel through a series of chemical reactions. Following formation of the gel, the impression is removed from the mouth for use in the construction of dental forms.

The basic ingredients of an illustrative powdered alginate comprise potassium alginate, calcium sulfate dihydrate, trisodium phosphate and diatomaceous earth, to which there may be added special purpose ingredients such as magnesium oxide and potassium titanium flouride as well as ingredients for color, flavor and preservation.

The significant ingredient in the powdered alginate composition is soluble potassium alginate which is derived from sea kelp. When the powdered alginate composition is mixed with water, the soluble alginate reacts with the calcium sulfate to produce the gel structure of an insoluble calcium alginate. Since this reaction must take place and go to completion in the mouth, it must be delayed until the aqueous composition is placed in the impression tray and carried to the mouth. In order to effect this delay and provide adequate working time, a reaction rate retarder such as trisodium phosphate is incorporated into the composition. The suggested mechanism for the effectiveness of the reaction rate retarder is that the calcium sulfate will react first with the trisodium phosphate before reacting with the soluble alginate and that as long as any trisodium phosphate is present, the gelling reaction between the soluble alginate and the calcium sulfate will be prevented. A filler such as diatomaceous earth is also incorporated into the formulation to increase the strength and stiffness of the gel and to provide a firm surface that is not tacky. The final structure of the gel is characterized as a brush-heat network of fibrils of calcium alginate which holds the excess water, filler and other ingredients.

The following prior art patents illustrate the state of the art with respect to settable alginate compositions:

U.S. Pat. No. 2,657,971 (Lochridge, 1953) discloses the use of tetrasodium salt of ethylene diamine tetra acetic acid as a reaction rate retarder in a powdered alginate composition containing, for example, potassium alginate, calcium sulfate, diatomaceous earth and sodium fluosilicate.

U.K. Pat. No. 936,091 (Lonsdale, 1963) discloses that dimensionally stable impressions can be obtained by the use of sodium flouride and potassium fluorortitanate in a powdered alginate composition containing sodium alginate, calcium sulfate dihydrate, sodium tripolyphosphate, diatomaceous earth and a blend of light and ultralight magnesium oxide.

U.K. Pat. No. 951,547 (Nordin, 1964) discloses that dimensionally stable impressions can be obtained by the addition of powdered aluminum to a powdered alginate composition containing sodium alginate, calcium sulfate, sodium flouride, zinc oxide, magnesium oxide, sodium tripolyphosphate, and diatomaceous earth as well as lead silicate.

U.S. Pat. No. 3,268,348 (Morrell, 1966) and U.K. Pat. No. 1,159,471 (Morrell, 1969) disclose, respectively, the use of barium fluoride and lithium fluoride in powdered alginate compositions containing potassium alginate, calcium sulphate dihydrate, tetrasodium pyrophosphate, magnesium oxide and diatomaceous earth whereby impressions made therefrom do not require any treatment in an aqueous fixing bath containing an inorganic salt and that models or casts produced from such impressions possess hard smooth surfaces, which are free from chalkiness and dusting in handling during use of the same or in storage.

U.K. Pat. No. 1,365,024 (Marrickville Holdings Ltd., 1974) discloses that dental impression material having improved flexibility and strength can be prepared from powdered alginate compositions containing potassium alginate, tetrasodium, pyrophosphate, sodium silicofluoride, sodium metasilicate, sodium fluoride, zinc fluoride and synthetic calcium sulfate comprising a blend of calcium sulfate hemihydrate and calcium sulfate dihydrate.

U.S. Pat. No. 4,381,947 (Pellico, 1983) discloses an interactable, two-component, paste system for preparing alginate impression material wherein one component contains an alkali metal alginate in an aqueous paste and the other component contains a divalent metal salt such as calcium sulfate and a reaction rate retarder such as tetrasodium pyrophosphate in a fluid plasticizer that is substantially free of unbound water.

The powdered alginate compositions of the prior art, upon admixing with water to form dental impression material, tend to appear grainy and form lumps. This phenomena is primarily associated with the alkali metal alginate ingredient. Accordingly, it would be advantageous to provide powdered alginate compositions which can be smoothly admixed with water without appearing grainy or forming lumps.

SUMMARY OF THE INVENTION

In accordance with one aspect of this invention, there is provided a powdered alginate composition that contains from about 0.5 to about 6.0 wt.% of polyacrylamide which provides a smooth admixture of the powdered alginate composition with water in the preparation of an orally, settable, dental impression material.

In accordance with a second aspect of this invention, there is provided a method for preparing an orally, settable, dental impression material which comprises admixing from about 2.0 to about 3.0 parts by weight of water with about 1.0 part by weight of powdered alginate composition that contains from about 0.5 to about 6.0 wt.% of polyacrylamide which improves the smoothness of the admixing step.

DETAILED DESCRIPTION

The polyacrylamides which can be used in this invention have a molecular weight from about 200,000 to about 6,000,000, and a carboxyl content that can vary from low to substantial. They can be dispersed, and dissolved, in cold water. The polyacrylamides typically take the form of dry powders. Polyacrylamide is generally present in the powdered alginate composition in an amount from about 0.5 to about 6.0 wt.% and, preferably, in an amount from about 1.0 to about 3.0 wt.%. The use of excess polyacrylamide should be avoided since such use tends to impair the strength of the alginate gel.

Polyacrylamides which are well suited for use in this invention include those which are available under the trademark CYANAMER from American Cyanamid Company, Chemical Products Division, Wayne, N.J., 07470 as, for example, CYANAMER P-250 identified as a homopolymer of acrylamide having a molecular weight of approximately 5,000,000 to 6,000,000, CYANAMER A-370 identified as modified polyacrylamide having a molecular weight of approximately 200,000 and a substantial carboxylate content, and CYANAMER P-26 identified as modified polyacrylamide having a molecular weight of approximately 200,000 and a low carboxyl content.

CYANAMER polyacrylamides are characterized as having diverse properties which make them useful in industrial application as chemical agents for thickening, binding, solubilizing, dispersing, flocculating, suspending, cross-linking, filtering, lubricating, drag reduction, flowability, crystal control, and polymer recovery.

While polyacrylamides, which are characterized as having thickening and stabilizing properties, are particularly effective in improving the aqueous mixing characteristics of the powdered alginate composition, it has been found that other additives, which are also identified as having thickening and stabilizing properties, do not impart any improved smoothness during admixing of the powdered alginate composition with water. In particular, it has been found that additives such as locust-bean gum, karaya gum, tragacanth gum, corn starch, polyvinyl alcohol, polyoxyethylene, and fructose when incorporated into the powdered alginate compositions do not improve the smoothness of the aqueous mixing step.

The powdered alginate compositions, which are improved by adding polyacrylamides thereto, typically contain an alkali metal alginate, calcium sulfate, a phosphate, a fluoride, magnesium oxide, color and flavor ingredients, and a filler.

The alkali metal alginates which can be used include sodium alginate, potassium alginate and mixtures thereof. The alginate is generally present in the powdered composition in an amount from about 6 to about 10 wt.% and, preferably, in an amount from about 8 to about 9 wt.%. The calcium sulfate reactant is, preferably, calcium sulfate dihydrate which is known commercially as terra alba. Calcium sulfate dihydrate is generally present in the powdered composition in an amount from about 6 to about 12 wt.% and, preferably, in an amount from about 7 to about 11 wt.%. The reaction rate retarders which can be utilized in the invention include, for example, tetrasodium pyrophosphate, sodium tripolyphosphate and mixtures thereof. The phosphate retarder is generally present in the powdered composition in an amount from about 0.6 to about 1.2 wt.% and, preferably, in an amount from about 0.7 to about 1.1 wt.%. The fluoride constituent of the composition may be an alkali metal fluoride but, preferably, is a double metal fluoride salt such as potassium titanium fluoride, potassium zinc fluoride and the like. The fluoride constituent is generally present in the composition in an amount from about 1 to about 3 wt.%, and, preferably, in an amount from about 1.5 to about 2.5 wt.%. The magnesium oxide component may be light magnesium oxide or a mixture of light and heavy magnesium oxide. The magnesium oxide component is generally present in the composition in an amount from about 2 to about 6 wt.% and, preferably, in an amount from about 3 to about 5 wt.%. Color, flavor and preservative ingredients can be present in trace amounts. A filler such as diatomaceous earth is included in the composition in an amount to make up 100 wt.%.

In use, about 1.0 parts by weight of the polyacrylamide modified powdered alginate composition is admixed, by spatulation, with about 2.0 to about 3.0 parts by weight of water and, preferably, with about 2.2 to about 2.8 parts by weight of water to attain a smooth, paste-like, dental impression material. Spatulation of the aqueous mix may take place in about one half to one minute, and it is then transferred to an impression tray which is applied to a dental area in the mouth where an impression is to be taken. The formulation of the orally, settable, dental impression material is so designed that it sets in the mouth in about three and one-half to about four minutes. Upon completion of the impression taking step, the impression material is removed from the mouth and used in the preparation of a "stone" cast or model. A suitable plaster of Paris composition made up to proper consistency with water may be used in making the stone cast or model.

EXAMPLES

The following examples (a) illustrate the aqueous mixing characteristics of the prior art powdered alginate compositions, (b) demonstrate that many additives identified as being stabilizers do not have any significant effect on the aqueous mixing properties of powdered alginate compositions, and (c) show varying concentration levels and molecular weights for the polyacrylamides which can be advantageously used to markedly improve the aqueous mixing characteristics of powdered alginate compositions.

The powdered alginate compositions set out in the examples were prepared and evaluated by taking 20 grams of the blended mixture and admixing the same, by spatulation, with 50 grams of water for about 30 seconds and observing the aqueous mixing characteristics. The CYANAMER trademark used in the examples identify those polyacrylamides which have been hereinabove described.

EXAMPLE 1

This example illustrates the aqueous mixing characteristics of typical prior art powdered alginate compositions.

| INGREDIENTS | PARTS BY WEIGHT | |
|---|---|---|
| | 1(a) | 1(b) |
| Sodium alginate | 8.5 | — |
| Potassium alginate | — | 8.5 |
| Calcium sulfate dihydrate | 10.0 | 10.0 |
| Tetrasodium pyrophosphate | 1.0 | 1.0 |
| Potassium titanium fluoride | 1.0 | 1.0 |
| Magnesium oxide | 4.0 | 4.0 |
| Color | 0.5 | 0.5 |
| Diatomaceous earth | 76.0 | 76.0 |

Compositions 1(a) and 1(b) were relatively difficult to mix with water; and the aqueous mix was not smooth and creamy and, in addition, contained some undissolved lumps and powder.

EXAMPLE II

This example illustrates the aqueous mixing characteristics of powdered alginate compositions formulated with various gums that are identified in the literature as having stabilizing properties.

| INGREDIENTS | PARTS BY WEIGHT | | | |
|---|---|---|---|---|
| | 2(a) | 2(b) | 2(c) | 2(d) |
| Sodium alginate | 8.5 | 8.5 | 8.5 | 8.0 |
| Calcium sulfate dihydrate | 10.0 | 10.0 | 10.0 | 10.0 |
| Tetrasodium pyrophosphate | 1.0 | 1.0 | 1.0 | 1.0 |
| Potassium titanium fluoride | 1.0 | 1.0 | 1.0 | 1.0 |
| Magnesium oxide | 4.0 | 4.0 | 4.0 | 4.0 |
| Color | 0.5 | 0.5 | 0.5 | 0.5 |
| Diatomaceous earth | 75.0 | 75.0 | 75.0 | 75.0 |
| Karaya gum | 1.0 | — | — | — |
| Tragacanth gum | — | 1.0 | — | — |
| Locust-Bean gum | — | — | 1.0 | 5.0 |

The addition of karaya gum or tragacanth gum or locust-bean gum to the powdered alginate compositions of the prior art did not improve the smoothness characteristics of aqueous mix which continued to appear grainy and contain lumps.

EXAMPLE III

In this example, diverse additives were evaluated for their effect on the aqueous mixing characteristics of powdered alginate compositions.

| INGREDIENTS | PARTS BY WEIGHT | | | |
|---|---|---|---|---|
| | 3(a) | 3(b) | 3(c) | 3(d) |
| Sodium alginate | 8.5 | 8.5 | 8.5 | — |
| Potassium alginate | — | — | — | 8.5 |
| Calcium sulfate dihydrate | 10.0 | 10.0 | 10.0 | 10.0 |
| Tetrapotassium pyrophosphate | 1.0 | 1.0 | 1.0 | 1.0 |
| Potassium titanium fluoride | 1.0 | 1.0 | 1.0 | 1.0 |
| Magnesium oxide | 4.0 | 4.0 | 4.0 | 4.0 |
| Color | 0.5 | 0.5 | 0.5 | 0.5 |
| Diatomaceous earth | 75.0 | 75.0 | 75.0 | — |
| Polyvinyl alcohol | 1.0 | — | — | — |
| Fructose | — | 1.0 | — | — |
| Polyoxyethylene | — | — | 1.0 | — |
| Corn starch | — | — | — | 0.5 |
| Silicon dioxide | — | — | — | 75.0 |

The addition of polyvinyl alcohol or fructose or polyoxyethylene or corn starch to the powdered alginate compositions of the prior art did not improve the smoothness characteristics of the aqueous mix.

EXAMPLE IV

This example illustrates the aqueous mixing characteristics of powdered alginate compositions which contain polyacrylamide.

| INGREDIENTS | PARTS BY WEIGHT | | | |
|---|---|---|---|---|
| | 4(a) | 4(b) | 4(c) | 4(d) |
| Potassium alginate | 8.5 | 8.5 | 8.5 | 8.5 |
| Calcium sulfate dihydrate | 10.0 | 10.0 | 10.0 | 10.0 |
| Tetrasodium pyrophosphate | 1.0 | 1.0 | — | — |
| Tetrapotassium pyrophosphate | — | — | 1.0 | 1.0 |
| Potassium titanium fluoride | 1.0 | 1.0 | 1.0 | 1.0 |
| Magnesium oxide | 4.0 | 4.0 | 4.0 | 4.0 |
| Color | 0.5 | 0.5 | 0.5 | 0.5 |
| Diatomaceous earth | 75.0 | 74.0 | 73.0 | 74.0 |
| CYANAMER P-250 | 0.5 | 1.5 | 2.5 | 1.0 |
| Polyox WSN-10 | — | — | — | 0.3 |

The addition of polyacrylamide (CYANAMER P-250) to the powdered alginate compositions of the prior art substantially improved the mixing characteristics of the aqueous mix in that the aqueous mix did not appear grainy or form lumps. This example also demonstrates that polyacrylamide may be used to bring other water soluble gums such as Polyox WSN-10 polyoxyethylene into smooth solution with powdered alginates. The compositions were evaluated for gel strength and it was noted that the gel strength of composition 4(c) was less than that of the other compositions of this example.

EXAMPLE V

This example illustrates the use of CYANAMER A-370 and CYANAMER P-26 polyacrylamides in powdered alginate compositions as well as the use of surfactants and dust suppressors in such compositions.

| INGREDIENTS | PARTS BY WEIGHT | |
|---|---|---|
| | 5(a) | 5(b) |
| Potassium alginate | 10.0 | 10.0 |
| Calcium sulfate dihydrate | 11.0 | 11.0 |
| Sodium tripolyphosphate | 1.5 | — |
| Trisodium phosphate | — | 1.6 |
| Potassium titanium fluoride | 2.0 | 2.0 |
| Magnesium oxide | 6.0 | 6.0 |
| CYANAMER A-370 | 5.0 | — |
| CYANAMER P-26 | — | 4.0 |
| Diatomaceous earth | 62.0 | 63.0 |
| Color | 0.5 | 0.5 |
| Flavor/preservative | Trace | Trace |
| Nonionic surfactant | Trace | Trace |
| Dust suppressor | 1.0 | 1.0 |

In view of the foregoing description and examples it will become apparent to those of ordinary skill in the art that equivalent modifications thereof may be made That which is claimed is:

1. In a powdered alginate, dental impression composition that is adapted to be mixed with water and is orally settable said powdered alginate composition containing:

from about 6 to about 10 wt.% of an alkali metal alginate selected from the group consisting of sodium alginate, potassium alginate and mixtures thereof, from about 6 to about 12 wt.% of a calcium sulfate reactant, from about 0.6 to about 1.2 wt.% of a reaction rate retarder selected from the group consisting of phosphate, pyrophosphate and tripolyphosphate salts of sodium, potassium and mixtures thereof, and a filler, the improvement which comprises polyacrylamide in said powdered alginate composition in an amount from about 0.5 to about 6.0 wt.% to thereby effect a smooth admixture of the powdered alginate composition with water.

2. The powdered alginate composition of claim 1 wherein the polyacrylamide is present in an amount from about 1.0 to about 3.0 wt.%.

3. The powdered alginate composition of claim 1 wherein the molecular weight of the polyacrylamide is from about 200,000 to about 6,000,000.

4. The powdered alginate composition of claim 1 wherein the polyacrylamide is a homopolymer of acrylamide having a molecular weight from about 5,000,000 to about 6,000,000.

5. The powdered alginate composition of claim 1 wherein the polyacrylamide has a molecular weight of about 200,000.

6. In a method for preparing an orally settable, dental impression material which comprises admixing from about 2.0 to about 3.0 parts by weight of water with about 1.0 part by weight of a powdered alginate composition containing:

from about 6 to about 10 wt.% of an alkali metal alginate selected from the group consisting of sodium alginate, potassium alginate and mixtures thereof, from about 6 to about 12 wt.% of a calcium sulfate reactant, from about 0.6 to about 1.2 wt.% of a reaction rate retarder selected from the group consisting of phosphate, pyrophosphate and tripolyphosphate salts of sodium, potassium and mixtures thereof, and a filler, the improvement which comprises incorporating polyacrylamide into said powdered alginate composition in an amount from about 0.5 to about 6.0 wt.% to thereby effect a smooth admixture of the powdered alginate composition with said water.

7. The method of claim 6 wherein from about 2.2 to about 2.8 parts by weight of water is admixed with about 1.0 part by weight of powdered alginate composition.

8. The method of claim 6 wherein the powdered alginate composition contains from about 1.0 to about 3.0 wt.% of polyacrylamide.

9. The method of claim 6 wherein the molecular weight of the polyacrylamide is from about 200,000 to about 6,000,000.

10. The method of claim 6 wherein the polyacrylamide is a homopolymer of acrylamide having a molecular weight from about 5,000,000 to about 6,000,000.

11. The method of claim 6 wherein the polyacrylamide has a molecular weight of about 200,000.

* * * * *